(12) United States Patent
Hertenberger et al.

(10) Patent No.: US 7,393,936 B2
(45) Date of Patent: Jul. 1, 2008

(54) METHOD FOR THE RECOMBINANT PRODUCTION AND PURIFICATION OF PROTEIN KINASES

(75) Inventors: Hubert Hertenberger, Weilheim (DE); Konrad Honold, Penzberg (DE); Christian Klein, Iffeldorf (DE); Petra Rueger, Penzberg (DE)

(73) Assignee: Hoff Hoffmann-La Roche Inc., Nutley, NJ (US)

( * ) Notice: Subject to any disclaimer, the term of this patent is extended or adjusted under 35 U.S.C. 154(b) by 262 days.

(21) Appl. No.: 11/000,867

(22) Filed: Dec. 1, 2004

(65) Prior Publication Data

US 2005/0282250 A1    Dec. 22, 2005

(30) Foreign Application Priority Data

Dec. 2, 2003    (EP) ............................ 03027755

(51) Int. Cl.
C07K 1/02    (2006.01)
C07K 1/14    (2006.01)
C07K 1/20    (2006.01)
C12N 9/12    (2006.01)
C12N 15/70   (2006.01)

(52) U.S. Cl. ............... 530/412; 530/414; 435/69.1; 435/194; 435/320.1

(58) Field of Classification Search ............... None
See application file for complete search history.

(56) References Cited

U.S. PATENT DOCUMENTS

| 5,336,615 | A * | 8/1994 | Bell et al. ............... 424/423 |
| 6,005,081 | A * | 12/1999 | Burton et al. ............. 530/399 |
| 6,184,360 | B1 * | 2/2001 | Burton et al. ............. 530/399 |
| 6,423,831 | B1 * | 7/2002 | Burton et al. ............. 530/399 |
| 6,812,330 | B2 * | 11/2004 | Burton et al. ............. 530/399 |
| 6,900,034 | B2 * | 5/2005 | Suck et al. ............... 435/69.1 |
| 2005/0249701 | A1 * | 11/2005 | Morre et al. ............. 424/85.2 |

FOREIGN PATENT DOCUMENTS

| WO | WO 03/016516 | 2/2003 |
| WO | WO 03/097669 | * 11/2003 |

OTHER PUBLICATIONS

Werber, M.M., et al., 1991, "Large-scale purification and refolding of recombinant proteins derived from fibronectin domains", Biology of Recombinant Microorganism and Animal Cells, vol. 34 (Meeting), pp. 369-382.*

(Continued)

*Primary Examiner*—Nashaat T. Nashed
*Assistant Examiner*—William W. Moore
(74) *Attorney, Agent, or Firm*—George W. Johnston; Patricia S. Rocha-Tramaloni

(57) ABSTRACT

A method for the recombinant production and purification of a protein kinase selected from the group consisting of tyrosine protein kinases and serine/threonine kinases by expressing a nucleic acid encoding said kinase in a microbial host cell, forming inclusion bodies containing said kinase, isolating, solubilizing, naturing, and purifying said kinase wherein said purification is performed by hydrophobic interaction with an hydrophobic adsorbent under conditions whereby at least 70% of said protein kinase are not bound to said adsorbent and the protein kinase not bound to said adsorbent is recovered.

12 Claims, 3 Drawing Sheets

OTHER PUBLICATIONS

Arakawa, T. et al., 1993, "Production and characterization of an analog of acidic fibroblast growth factor with enhanced stability and biological activity", Protein Engineering, vol. 6, No. 5, pp. 541-546.*

Breton, J., et al., 1995, "Structure, stability, and biological properties of a N-terminally truncated form of recombinant human interleukin-6 containing a single disulfide bond", European Journal of Biochemistry, vol. 227, pp. 573-581.*

Oda, Y., et al., 1999, "cSrc is a major cytosolic tyrosyne kinase in vascular tissue", Canadian Journal of Physiology and Pharmacology, vol. 77, No. 8, pp. 606-617.*

Moellering, B.J., et al., 1999, "Folding and purification of a recombinantly expressed interferon regulatory factor, IRF-4", Protein Expression and Purification, vol. 16, pp. 160-170.*

Thies, M.J.W., & Pirkl, F., 2000, "Chromatographic purification of the CH2 domain of the monoclonal antibody MAK33", Journal of Chromatography B, vol. 737, pp. 63-69.*

Johnson, T.M., et al., 2000, "Expression of functional recombinant scorpion beta-neurotoxin Css II in *E. coli*", Peptides, vol. 21, pp. 767-772.*

Hsieh, M.-C., & Cooperman, B.S., 2000, "The preparation and catalytic properties of recombinant human prostate-specific antigen (rPSA)", Biochimica et Biophysica Acta, vol. 1481, pp. 75-87.*
Guo, L.-A., 2001, "Simultaneous purification and renaturation of recombinant human interferon-alpha expressed by *E. coli* by high-performance hydrophobic interaction chromatography", Chinese Journal of Chromatography, vol. 19, No. 4, pp. 301-303 and English language abstract.*
Ferre, H., et al., Mar. 2003, "Purification of correctly oxidized MHC class I heavy-chain molecules under denaturaing conditions: A novel stratgy exploiting disulfice assisted protein folding", vol. 12, pp. 551-559.*
2002 Amersham Biosciences product catalogue, pp. 544, 545, and 549.*
Brazil, D.P. & Hemmings, B.A., *Trends Biochem. Sci.*, 11 (2001) 657-664.
Clark, E.D., *Curr. Opin. Biotechnol.*, 12 (2001) 202-207.
Datta, S.R. et al, *Genes Dev.* 13 (1999) 2905-2927.
Egan, S.E. & Weinberg, R.A., *Nature* 365 (1993) 781-783.
Hardie, G., & Hanks, S., *The Protein Kinase Facts Books I*, Academic Press, 1995, pp. 7-20.
Hunter, T., *Cell* 50 (1987) 823-829.
Lee, S.Y, *TrendsBiotechnol.* 14 (1996) 98-105.
Lilie, H., *Current Opinion Biotechnol.*, 9 (1998) 497-501.
Mattes, R., *Semin. Thromb. Hemost.*, 27 (2001) 325-335.
Misawa, S. & Kumagai, I., *Biopolymers* 51 (1999) 297-307.
Panda, A.K. et al, *Biotechnol.*, 75 (1999) 161-172.
Thomas, S.M. & Brugge, J.S., *Annu. Rev. Cell Dev. Biol.* 13 (1997) 513-609.
Clark, E.D., *Current Opin. In Biotech.*, 9:2 (1988) 157-162.
Ouellette T. et al, *Protein Expression and Purification, Academic Press*, 30:2, (Aug. 2003) 156-166.
Caspers, P. et al, *Cellular and Molecular Biology, CMB Assoc.*, 40:5 (1994) 635-644.
Keesler, G.A., et al, *Protein Expression and Purification, Academic Press*, 14:2 (1998) 221-228.
Jullien, P. et al, *European Journal of Biochemistry*, 224:2 (1994) 589-596.
Shi et al, *Biotechniques*, 23:6 (1997) 1036-1038.
Suttnar, J. et al, *Journal of chromatography B: Biomedical Appl., Elsevier Sci. Publishers, NL*, 656:1 (1994) 123-126.
Lin, W.J. et al, *Protein Expression and Purification*, 4:3 (1993) 256-264.
Pav, S. et al, *Protein Sci*, 6:1 (1997) 242-245.
Li Ming, et al., *Separation and identification of different refolding components*, Journal of Biotechnology, vol. 103, No. 2, pp. 119-127 (2003), XP002321231.

* cited by examiner

METHOD FOR THE RECOMBINANT PRODUCTION AND PURIFICATION OF PROTEIN KINASES

BACKGROUND OF THE INVENTION

Protein kinases regulate many different cell proliferation, differentiation, and signaling processes by adding phosphate groups to proteins (Hunter, T., Cell 50 (1987) 823-829). Protein kinases are usually named after their substrate, their regulatory molecules, or some aspect of a mutant phenotype. With regard to substrates, the protein kinases may be divided into two groups; those that phosphorylate tyrosine residues (protein tyrosine kinases, PTK) and those that phosphorylate serine or threonine residues (serine/threonine kinases, STK). Almost all kinases contain a similar 250-300 amino acid catalytic domain. The N-terminal domain binds and orients the ATP (or GTP) donor molecule. The larger C terminal part binds the protein substrate and carries out the transfer of phosphate from ATP to the hydroxyl group of a serine, threonine, or tyrosine residue.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contain specific residues and motifs or patterns of amino acids that are characteristic of that subdomain and are highly conserved (Hardie, G., and Hanks, S., The Protein Kinase Facts Books I, Academic Press, San Diego, Calif., 1995, pp. 7-20).

The second messenger dependent protein kinases primarily mediate the effects of second messengers such as cyclic AMP (cAMP) cyclic GMP, inositol triphosphate, phosphatidylinositol, 3,4,5-triphosphate, cyclic ADP ribose, arachidonic acid and diacylglycerol. Cyclic -AMP dependent protein kinases (PKA) and mitogen-activated protein kinases (MAPK) are e.g. members of the STK family. Cyclic -AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic -AMP in most of these cells. Altered PKA expression is implicated in a variety of disorders and diseases including cancer, thyroid disorders, diabetes, atherosclerosis, and cardiovascular disease.

MAP kinases like p38 also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E., and Weinberg, R. A., Nature 365 (1993) 781-783).

Protein kinase B (PKB/Akt) is a component of an intracellular signalling pathway of fundamental importance that functions to exert the effects of growth and survival factors, and which mediates the response to insulin and inflammatory signals (Datta, S. R., et al., Genes Dev. 13 (1999) 2905-2927; Brazil, D. P., and Hemmings, B. A., Trends Biochem. Sci. 11 (2001) 657-664). The recombinant production and purification of PKB is described in WO 2003/016516 using Phenyl TSK hydrophobic interaction chromatography. PKB was adsorbed to the column and eluted after washing PKB using a linear gradient.

Src kinases are implicated in cancer, immune system dysfunction and bone remodeling diseases. For general reviews, see Thomas, S. M., and Brugge, J. S., Annu. Rev. Cell Dev. Biol. 13 (1997) 513-609. Members of the Src family are e.g. Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal 15 regulatory region.

In prokaryotic organisms, the protein synthesis, also referred to as translation, takes place on the ribosomes in the cytoplasm. In expressing recombinant DNA in prokaryotic host organisms, such as, e.g., E. coli the resultant recombinant gene product/protein often precipitates in the cytoplasm in the form of insoluble inclusion bodies. After completion of fermentation and lysis of the cells, the inclusion bodies are isolated and optionally purified and the recombinant protein contained therein is solubilized by adding denaturants such as urea or guanidinium hydrochloride and naturation of said protein is accomplished by reducing the denaturing conditions. Such methods are well-known and have long been used successfully also for the industrial manufacture of recombinant proteins (cf., e.g., Lee, S. Y., Trends Biotechnol. 14 (1996) 98-105; Panda, A. K., et al., J. Biotechnol. 75 (1999) 161-172; Mattes, R., Semin. Thromb. Hemost. 27 (2001) 325-336; Clark, E. D., Curr. Opin. Biotechnol. 12 (2001) 202-207; Misawa, S., and Kumagai, I., Biopolymers 51 (1999) 297-307; and Lilie, H., Current Opinion Biotechnol. 9 (1998) 497-501).

However, expression of mammalian proteins in microbial host cells like E. coli is often a challenging task due to poor solubility, improper folding, lack of stability and other problems. Past attempts to produce such protein kinases by recombinant expression in microbial host cells pursuant to known methods in the art generally result in general only low amounts of active soluble kinases but with large amounts of undesired and inactive dimers and higher aggregates.

Now it was surprisingly found, that using the method of the invention kinases can be recovered after recombinant production in microbial host cells in a correctly folded form in large amounts.

SUMMARY OF THE INVENTION

The invention relates to an improved method for the recombinant production and purification of protein kinases in prokaryotes via inclusion bodies.

The object of the invention therefore is a method for the recombinant production and purification of a protein kinase selected from the group consisting of tyrosine protein kinases and serine/threonine kinases comprising a) expressing a nucleic acid encoding said kinase in a microbial host cell, b) forming inclusion bodies containing said protein kinase, and c) isolating, solubilizing, naturing, and purifying said protein kinase wherein said purification is performed by hydrophobic interaction with an hydrophobic adsorbent under conditions whereby at least 70% of said correctly folded protein kinase are not bound to said adsorbent and the protein kinase not bound to said adsorbent is recovered and unfolded protein is bound to the adsorbent.

Preferably said protein kinase is Src, PKB, c-Met, Llck, Aurora or p38 MAPK.

The adsorbent according to the invention comprises a solid or gel material, perferably a solid or gel material comprising cellulose, cross-linked dextran, cross-linked agarose or the like modified with hydrophobic residues like phenyl-, butyl-, or octylresidues (HIC adsorbent, hydrophobic interaction chromatography adsorbent).

Preferably the kinase is treated with the hydrophobic adsorbent in an aqueous solution comprising at least 0.1 M, more preferably at least 1M of a salt wherein the salt preferably comprises a cation, selected from the group consisting of sodium, potassium and ammonium, and an anion selected from the group consisting of chloride, sulfate (except not with ammonium) and phosphate, more preferably NaCl or KCl. Higher salt concentrations are possible as long as the protein kinase does not bind in an undesired large amount exceeding 70% of the total amount of protein kinase protein material, wherein the total amount of protein kinase material includes the correctly folded protein kinase, the not correctly folded protein kinase aggregates, and other undesired protein kinase material. In addition high salt concentrations (e.g., above 5M) may destabilze and/or denature protein kinases.

In addition the above hydrophobic interaction treatment is performed preferably in the presence of at least about 0.5 M arginine, guanidine or a compound comprising the general formula I $$R_2\text{—CO—NRR}_1 \qquad (I),$$

or combination thereof, wherein

R and $R_1$ are hydrogen or a saturated or unsaturated branched or unbranched $C_1$-$C_4$ alkyl chain and $R_2$ is hydrogen, $NHR_1$ or a saturated or unsaturated branched or unbranched $C_1$-$C_3$ alkyl chain.

DETAILED DESCRIPTION OF THE INVENTION

Figure 1:
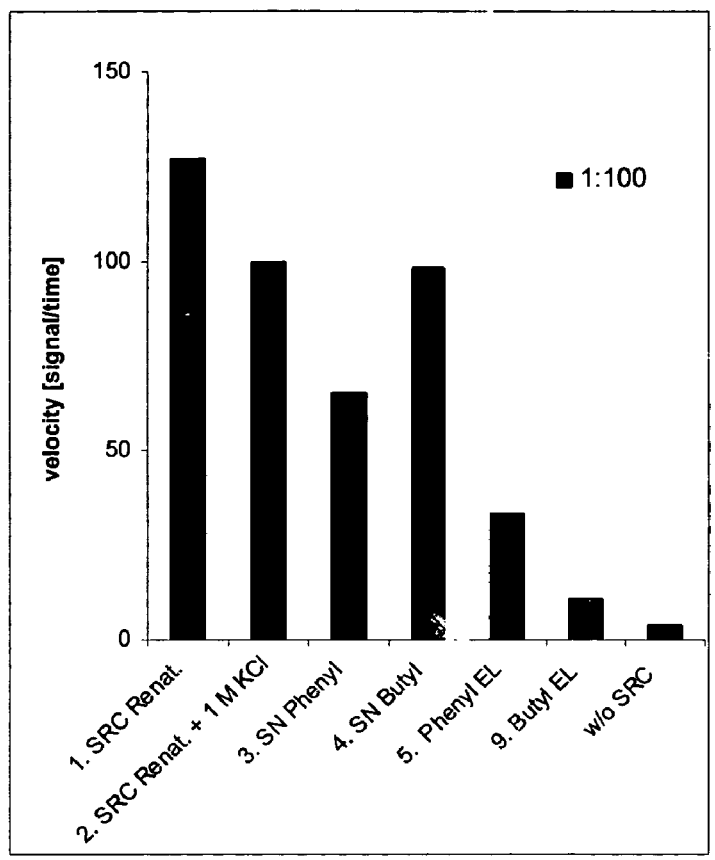
FIG. 1: Src activity after renaturation and hydrophobic chromatography as described. Activity is found in supernatant (SN) (EL=eluate).

The invention relates to an improved method for the recombinant production and purification of protein kinases in prokaryotes via inclusion bodies.

The object of the invention therefore is a method for the recombinant production and purification of a protein kinase selected from the group consisting of tyrosine protein kinases and serine/threonine kinases comprising a) expressing a nucleic acid encoding said kinase in a microbial host cell, b) forming inclusion bodies containing said protein kinase, and c) isolating, solubilizing, naturing, and purifying said protein kinase wherein said purification is performed by hydrophobic interaction with an hydrophobic adsorbent under conditions whereby at least 70% of said correctly folded protein kinase are not bound to said adsorbent and the protein kinase not bound to said adsorbent is recovered and unfolded protein is bound to the adsorbent.

Preferably said protein kinase is Src, PKB, c-Met, Lck, Aurora or p38 MAPK.

The adsorbent according to the invention comprises a solid or gel material, preferably a solid or gel material comprising cellulose, cross-linked dextran, cross-linked agarose or the like modified with hydrophobic residues like phenyl-, butyl-, or octylresidues (HIC adsorbent, hydrophobic interaction chromatography adsorbent).

Preferably the kinase is treated with the hydrophobic adsorbent in an aqueous solution comprising at least 0.1 M, more preferred 1M of a salt wherein the salt preferably comprises a cation, selected from the group consisting of sodium, potassium and ammonium, and an anion selected from the group consisting of chloride, sulfate (except not with ammonium) and phosphate, more preferably NaCl or KCl. Higher salt concentrations are possible as long as the protein kinase does not bind in an undesired large amount exceeding 70% of the total amount of protein kinase protein material, wherein the total amount of protein kinase material includes the correctly folded protein kinase, the not correctly folded protein kinase aggregates, and other undesired protein kinase material. In addition high salt concentrations (e.g., above 5M) may destabilze and/or denature protein kinases.

In addition the above hydrophobic interaction treatment is performed preferably in the presence of at least about 0.5 M arginine, guanidine or a compound comprising the general formula I $$R_2\text{—CO—NRR}_1 \qquad (I),$$

or combinations thereof, wherein

R and R1 are hydrogen or a saturated or unsaturated branched or unbranched $C_1$-$C_4$ alkyl chain and $R_2$ is hydrogen, $NHR_1$ or a saturated or unsaturated branched or unbranched $C_1$-$C_3$ alkyl chain.

The protein kinases which can be produced and purified according to the invention have been defined above. Preferably the method according to the invention is useful for the production and purification of Src kinases and cyclic -AMP dependent protein kinases (PKA). Members of the Src family are e.g. Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal 15 regulatory region. Cyclic -AMP dependent protein kinases (PKA) are members of the STK family. Cyclic -AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic -AMP in most of these cells.

The above described protein kinases that can be produced according to the current invention all play an important role in biochemical processes. For further elucidation of metabolic correlations not only the natural protein kinases are of interest but also mutants of these naturally occuring protein kinases.

An adsorbent (HIC or hydrophobic adsorbent) useful according to the invention comprises preferably a gel matrix substituted with hydrophobic ligands. The degree of substitution is usually in the range of 10-50 µmol/ml gel. Preferred ligands are e.g. $C_2$-$C_8$ alkyl residues or simple aryl (like phenyl) residues. Usually hydrophobic interaction is increased by adding salt. If HIC adsorbents are used for chromatography the kinase in the correctly folded form is not bound to a considerable extent and therefore recovered in the flow-through.

Especially preferred is the use of a cross-linked agarose substituted with phenyl-, butyl- or octylgroups. Such adsorbent is for example phenyl-, butyl- or octyl-Sepharose (e.g. cross-linked agarose, 4% spherical, mean particle size 90 µm, particle size range 45-165 µm, degree of substitution approx. 50 µmol butyl groups/ml gel), available from Amersham Biosciences (General Electric Healthcare).

The treatment with the hydrophobic adsorbent can be performed according to methods known to one of ordinary skill in the art, e.g. treatment of the solution containing the kinase with a suspension of the adsorbent or as a chromatography (HIC). For example, the hydrophobic adsorbent is equilabraited in the renaturation buffer and added to the renaturation solution of the protein. The mixture is agitated, preferably in a cold storage room, for about one hour. The adsorbent is separated from the solution by filtration, such as for example plaited paper filter. Other chromatographic steps, such as for example ion exchange and size exclusion chromatography, optionally may be performed to achieve further purification.

The term "at least 70% of said protein kinase are not bound" means that from the protein recovered after recombinant production and naturation, which contains said protein kinase in a correctly folded form, not correctly folded form (e.g. multimers and the like) and other protein impurities from the host cell present in the aqueous solution containing the kinase, at least 70% of the correctly folded form are not bound to the adsorbent and found either in the supernant after treatment of the kinase solution with the adsorbent (the chromatographic material) or if the adsorbent (the chromatographic material) is used within a chromatographic HIC purification found in the flow-through.

The term "chromatographic material" as used herein refers to the material that is used for a purification process and more specifically comprises the adsorbent in the solution of the protein kinase. Preferably, the chromatogrpahic material comprises the use of the cross-linked agarose substituted with phenyl, butyl, or octyl groups, such as butyl-sepharose, in the solution of the protein kinase.

The term "correctly folded" means that the protein after naturation adopts the natural three dimensional structure. This is independent of catalytical activity and comprises also catalytically inactive mutants. Preferably active protein kinases are produced according to the current invention.

Binding of a correctly folded kinase to the adsorbent with a rate below 30% can be reached by treating an aqueous solution of such a kinase after naturation with at least 0.1 M of a salt solution, more preferably at least 1M of a salt, wherein the salt is selected from one or more of the group comprising of a cation selected from the group consisting of sodium, potassium, and ammonium, and an anion seelected from the group consisting of chloride, sulfate, and phosphate, except that where the cation is ammonium the anion is not sulfate. More preferably, the salt is KCl or NaCl Higher preferred salt concentrations are possible as long as the protein kinase do not bind in a undesired large amount exceeding 70% of the total amount of protein kinase protein material. In addition very high salt concentrations may destabilze protein kinases.

In a preferred embodiment of the invention, wherein the protein kinase is applied to a chromatogrpahic material in an aqueous solution containing at least 0.1 M of a salt, and more preferably, at least 1M of a salt, the aqueous solution contains (comprises) in addition at least 0.5 M of arginine, guanidine or a compound having the general formula I or combinations thereof. The aqueous solution containing in addition at least 0.5M arginine, guanidine or a compound having the general formula I or combinations thereof, preferably comprise one or more compounds selected from the group consisting of guanidine, arginine, general formula I compounds, and pharmaceutical salts of guanidine, arginine and general formula I compounds.

The compounds having the general formula I preferably comprise one or more compounds selected from the group consisting of formamide, acetamide, urea or urea derivatives, such as ethyl urea or methyl urea, and pharmaceutically acceptable salts of such compounds. The term guanidine comprises and includes the base guanidine as well as pharmaceutrically acceptable salts of guanidine. The term arginine comprises and includes the base arginine as well as pharmaceutically acceptable salts of arginine. For example, arginine can be used as a hydrochloride or as another titrated form of the base arginine. Preferably however L-arginine, more preferably the hydrochloride form of L-arginine, is employed.

Insoluble inclusion bodies are formed during recombinant expression of polypeptides in microbial host cells. Inclusion bodies are refractile aggregates of protease-resistant misfolded desired protein that occur upon over-expression of the encoding gene (Misawa, S., and Kumagai, I., Biopolymers 51 (1999) 297-307).

Suitable prokaryotic host cells for recombinant gene expression are, for example, gram-negative or gram-positive organisms, such as, e.g., *E. coli* and *Bacillus subtilis*. Suitable *E. coli* strains are, for instance, *E. coli* strains such as BL20, BL21, UT5600, AB101, XL1, K12, X1776 and W3110. However, other enterobacteriaceae as well as microorganisms such as *Klebsiella, Salmonella* or *Bacillus subtilis, Pseudomonas* or *Streptomyces* are also suitable as host cells. Also suitable as host cells are yeast strains, such as, e.g., *Saccharomyces, Pichia, Hansenula, Kluyveromyces* and *Schizosaccharomyces*.

The nucleic acid coding for the polypeptide is usually inserted in an expression vector. Suitable vectors are well-known to one skilled in the art and are, for example, plasmids or phages. See, e.g., "Sambook, J., Russel, D. W., Molecular Cloning, 3rd Edition, Chapter 15", relevant parts thereof are which hereby incorporated by reference.

The fermentation of the host cells is also accomplished according to methods known to one skilled in the art. After a predetermined number of cells has been reached (measured via the optical density of the fermentation broth/cell suspension), the expression of the recombinant polypeptide is induced and cultivation is performed until the stationary phase is reached (in the case of batch cultures). After completion of cell growth, the cells are harvested and the inclusion bodies are isolated and processed by solubilization and maturation according to known methods. Recovery of the correctly folded protein kinases from the solution, and not bound to the adsorbent, is according to methods known to those of ordinary skill in the art, depending upon the purity of the IB and intended use of the kinase. For example, as a first step the adsorbent is removed from the solution (e.g. via filtration, ultrafiltration, centrifugation etc). If further treatment steps are required the steps are varying. For example, for a change of the buffer salts dialysis may be employed. The protein kinase recovered afterwards is still in solution and can be further processed. If further purification steps follow, that don't require a concentrated protein solution, the recovered solution is directly applied, e.g. to a Ni-affinity-column. From this column the protein can be recovered as concentrated solution. If a step follows that needs a concentrated solution, e.g., a size-exclusion-chromatography, a concentration step, e.g, ultrafiltration, is inserted.

In general after the purification is finished the correctly folded protein kinase is recovered from the solution. Depending upon the ultimate product desired for the kinase, the solution may be even freeze dried, potentially after demineralization by e.g., dialysis or ion exchange, (for e.g., a desired protein powder) or a concentration step with ultrafiltration is applied (for e.g., a desired liquid formulation).

The invention provides therefore an improved method for the recombinant production and purification of a protein kinase selected from the group consisting of tyrosine protein kinases and serine/threonine kinases comprising: a) expressing a nucleic acid encoding said kinase in a microbial host cell, b) forming inclusion bodies containing said kinase, and c) isolating, solubilizing, naturing, and purifying said kinase, wherein said purification is performed by hydrophobic interaction with an hydrophobic adsorbent under conditions whereby at least 70% of said correctly folded protein kinase are not bound to said adsorbent and the protein kinase not bound to said adsorbent is recovered. With the method of the invention substantial amounts of correctly folded protein kinases can be recovered and purified up to a purity of about >90-95% and more.

The following examples, figures and references are provided to aid the understanding of the present invention, the true scope of which is set forth in the appended claims. It is understood that modifications can be made in the procedures set forth without departing from the spirit of the invention.

The following examples are provided for illustrative purposes and are not intended to limit the scope of applicants invention.

EXAMPLE 1

Recombinant Production of Src a) Cloning

Src kinase domain was cloned BamHI/HindIII into pQE32 (QIAGEN GmbH) with an N-terminal thrombin cleavage site introduced by PCR Constructs for the bacterial expression of mouse full length wild type Src kinase and derivatives for application in kinase assays and for structural purposes were cloned according to the following procedure.

The ORF coding for mouse full length Src kinase was amplified from cDNA plasmid pUSE Src wt (Upstate) via standard PCR using gene-specific oligonucleotide primers and Tgo/Taq DNA Polymeerases (Roche Diagnostics GmbH), and subsequently sub cloned via BamHI and HindIII restriction, sites into bacterial expression vector pQE32 (Qiagen GmbH). An N-terminal thrombin cleavage site was introduced by PCR. This vector served as a template for the generation of truncated and mutated versions of Src kinase domain and full lenth via site-directed mutagenesis. All inserts under control of the T5 promotor were confirmed by sequencing.

b) Fermentation

Vectors plus co-vector pUBS520 (Brinkmann, U., Mattes, R. E., Buckel, P., Gene 85 (1989) 109 114) were subsequently transformed into *E. coli* BL21 strain (Stratagene) for protein expression by large scale fermentation as inclusion bodies.

To prepare the inoculum 1 ml of a glycerol stock of the appropriate *E. coli* strain, harboring the expression plasmid to produce recombinant kinase protein, is added to 100 ml LB media and incubated for 8 to 10 hours on a rotary shaker at 37° C. This pre-culture is transferred to the sterilized fermenter vessel containing further LB media and glucose. The temperature of the main culture is maintained at 37° C. when insoluble expression of the kinase protein to inclusion bodies is desired. For example, proteins were expressed in *E. coli* BL21 grown at 37° C. in LB medium supplemented with ampicillin (100 µg/ml) to an absorbance of 0.5-0.8 before overnight induction at 37° C. with 0.5 mM IPTG (isopropl-D-thiogalactopyranoside). The dissolved oxygen concentration of the media throughout the fermentation is kept above 20% saturation by increasing the agitation speed. Additional feeding of the culture is performed with the addition of glucose at rising pH values and the continuous dosing of a yeast-tryptone solution (2 ml/min). The fed batch fermentation ends when no more increase of the optical density is measurable. The culture broth is harvested by centrifugation after incubation, resuspended and inclusion bodies are then prepared (Example 1, part c) according to the given procedure.

REFERENCES

Brinkmann, U., Mattes, R. E., Buckel, P., Gene 85 (1989) 109-114: High level expression of recombinant genes in *Escherichia coli* is dependent on the availability of the dnaY gene product.

c) IB Preparation

The biomass is suspended in a buffer containing Tris and $MgSO_4$. Lysozym and DNase (e.g. Benzonase from Merck) are added if required before disintegration of the cells of the biomass (bacteria cells). The bacteria cells are disrupted by homogenization to release the inclusion bodies from inside. Additional DNase keeps the suspension liquid what is essential for further handling. After an incubation period at room temperature a second buffer solution containing NaCl, EDTA and Brij solution is added to the suspension. The total incubation time is about one hour. The covered inclusion bodies are separated from the supernatant by centrifugation after an additional incubation time at room temperature. Then the pellet is suspended with a third buffer solution containing Tris and EDTA to wash the IBs (endotoxin release) and incubated under stirring at room temperature and centrifuged.

d) Naturation of Src 1.3 g inclusion bodies were suspended in 100 ml 0.1M TRIS pH 8.0, 8M Guanidin HCl, 10 mM EDTA, 10 mM DTT at room temperature. This Src solubilisate is added dropwise under stirring into 10 l refolding buffer containing 1M TRIS pH 7.0, 0.5M Arginine, 10 mM DTT, 10 tablets of Complete. The refolding process is continued 3-5 days at 8° C. without stirring.

Dialysis against different buffers commonly used in the prior art (acetate, phosphate, MES, TRIS pH 5-9 with various additives) at this stage was not successful due to high aggregation of inactive not corerctly folded Src and then co-immunoprecipitation of the active fraction. It was necessary to remove the inactive, not correctly folded Src solubilised in renaturation buffer by hydrophobic chromatography before dialysis.

e) Hydrophobic Batch Chromatography

Figure 2:
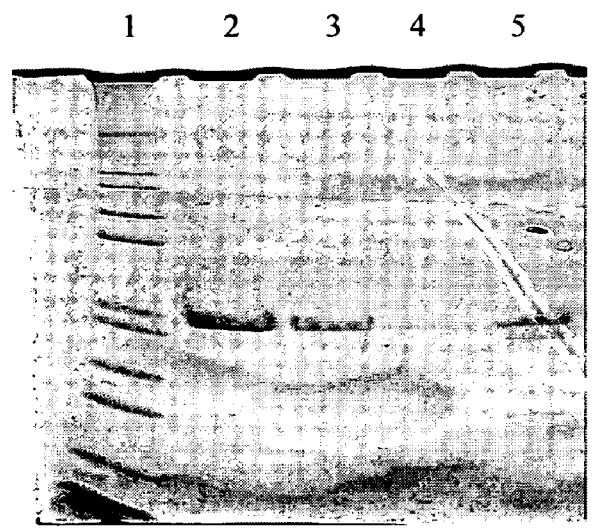
FIG. 2: SDS page of renaturation and butyl chromatography fractions, Coomassie stained. While retaining activity in butyl supernatant (SN) high amounts of inactive Src protein are cut off.
1: Molecular weight protein standard, 2: Renaturation, 3: Renaturation+KCl, 4: Butyl SN, 5: Ultrafiltration/concentration.

The refolded protein solution was set to 1M KCl. Subsequently 40 g Butylsepharose 4 Fast Flow (Amersham) were added and binding allowed for 1 h at 8° C. After removal of Butylsepharose by filtration the supernatant contains the correctly folded active Src protein. Under these conditions not correctly folded, non-active protein is bound to Butylsepharose. This method allows separation of active and inactive Src (FIGS. 1 and 2). Further purification can be achieved if necessary by additional chromatography steps i.e. Ni-chelate chromatography and size exclusion chromatography or other methods known to one of ordinary skill in the art, depending upon the subsequent intended application of the protein.

Figure 3:
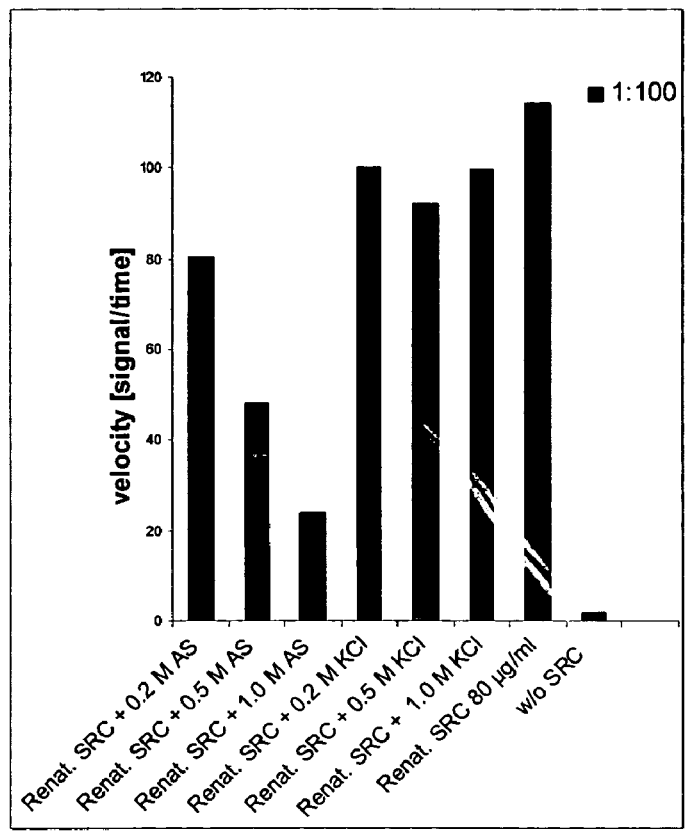
FIG. 3: Activity of Src after renaturation and addition of KCl or ammonium sulfate. Addition of ammonium sulfate that is common in hydrophobic chromatography results in loss of active-Src in supernatant. KCl up to 1M keeps active Src in solution and allows separation of inactive Src on Butyl sepharose.
Figure 4:
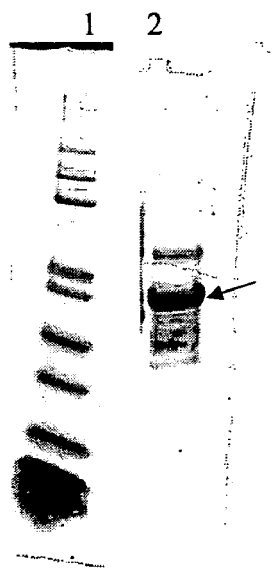
FIG. 4: SDS page, Coomassie Blue staining. Lane 1 standard proteins, lane 2 Aurora kinase preparation after refolding and Butyl Sepharose. Arrow: Aurora kinase.
Figure 5:
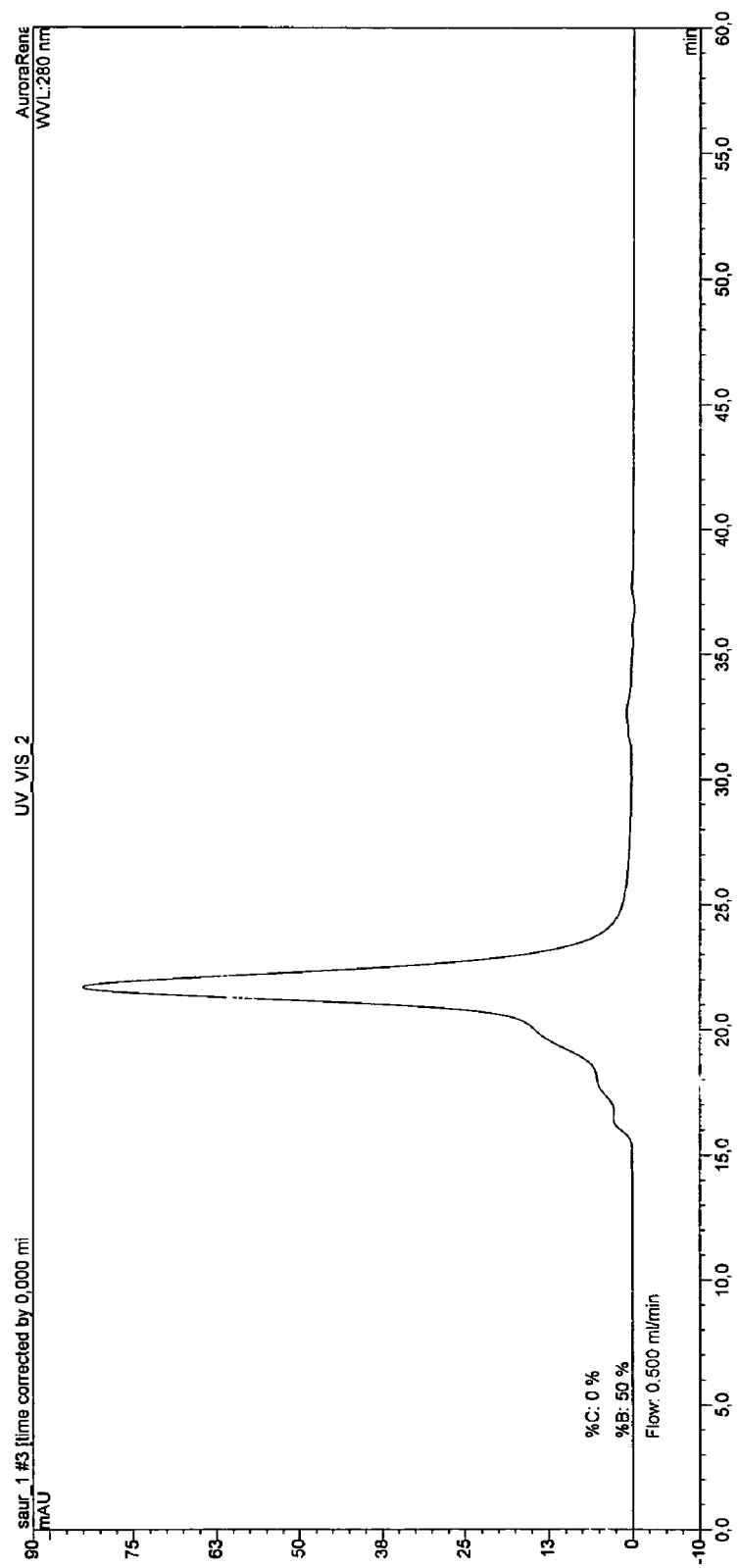
FIG. 5: Size exclusion chromatography of Aurora kinase after refolding and Butylsepharose batch. Superdex 75 (Pharmacia) 10/30. Buffer: 50 mM TRIS pH7.5, 500 mM NaCl, 10% Glycerol, 3 mM Chaps. Flow rate: 0.5 ml/min.

Addition of KCl (0.2M, 0.5M and 1.0M) proved to be superior versus ammonium sulfate as can be seen in FIG. 3. Similar concentrations of ammonium sulfate already result in precipitation of active Src. Using conditions that lead to binding of the active Src on hydrophobic materials were not suitable because of high loss of activity on the column. Eluates show only low Src protein and activity recovery.

f) Src Assay

Phosphorylation of Src substrate peptide YA133 labeled by Src kinase is measured by using a phosphotyrosine antibody Eu labeled (PT66 Lance Eu-W1024 (Wallac)) and detection of time resolved fluorescence signal.

EXAMPLE 2

Recombinant Production of Aurora a) Cloning

Vector constructs for the bacterial expression of human full-length wildtype Aurora A kinase and derivatives for application in kinase assays (e.g. Elisa, HTRF, FP) and for biostructural purposes were designed and cloned according to the following procedure.

The ORF coding for human full-length Aurora A kinase (residues 1-403) was amplified from a human HeLa cDNA library (Clontech) via standard PCR using gene-specific oligonucleotide primers and Pwo DNA polymerase (Roche Diagnostics GmbH), and subsequently subcloned into bacterial expression vectors. These vectors served as a template for the generation of truncated versions of Aurora A via PCR using gene-specific oligonucleotide primers and of Aurora A muteins via site-directed mutagenesis. For the final expression constructs wildtype and mutant Aurora A kinase domains (residues 114-403) were amplified from the corresponding Aurora A basic vectors via PCR using gene-specific primers and Pwo DNA polymerase. PCR products were subcloned via NdeI and XhoI restriction sites into modified pQE40 expression vectors under control of a T5 promoter with and without an N-terminal RGS-(His)$_6$-tag. All vector insert sequences were confirmed by sequencing. Vectors were subsequently transformed into E. coli BL21, 20 and UT5600 strains co-transformed with the pUBS520 co-repressor plasmid (Brinkmann, U., Mattes, R. E., Buckel, P., Gene. 85 (1989) 109-114). Aurora protein was subsequently expressed by large scale fermentation as inclusion bodies. Proteins were expressed in E. coli strains BL21 and UT5600 grown at 37° C. in LB medium supplemented with ampicillin (100 µg/ml) and kanamycin (50 µg/ml) to an absorbance of 0.5-0.8 before overnight induction at 37° C. with 1 mM isopropyl-D-thiogalactopyranoside. After induction, cells were harvested by centrifugation, resuspended and inclusion bodies were prepared according to the given procedure.

b) Fermentation

To prepare the inoculum 1 ml of a glycerol stock of the appropriate E. coli strain, harboring the expression plasmid to produce recombinant kinase protein, is added to 100 ml LB media and incubated for 8 to 10 hours on a rotary shaker at 37° C. This pre-culture is transferred to the sterilized fermenter vessel containing further LB media and glucose. The temperature of the main culture is maintained at 37° C. Additional feeding of the culture is performed with the addition of glucose at rising pH values and the continuous dosing of a yeast-tryptone solution (2 ml/min). The fed batch fermentation ends when no more increase of the optical density is measurable. The culture broth is harvested by centrifugation.

c) IB Preparation

The biomass is suspended in a buffer containing Tris and MgSO$_4$. Lysozym and DNase (e.g. Benzonase from Merck) are added if required. The bacteria cells are disrupted by homogenization to release the inclusion bodies from inside. After an incubation period at room temperature a second buffer solution containing NaCl, EDTA and Brij solution is added to the suspension. The covered inclusion bodies are separated from the supernatant by centrifugation after an additional incubation time at room temperature. Then the pellet is suspended with a third buffer solution containing Tris and EDTA to wash the IBs and incubated under stirring at room temperature and centrifuged.

d) Naturation of Aurora 160 mg inclusion bodies were suspended in 10 ml 0.1M TRIS pH 8.0, 8M Guanidin HCl, 10 mM EDTA, 10 mM DTT at room temperature. This aurora solubilisate is added dropwise under stirring into 1 l refolding buffer containing 1M TRIS pH 7.0, 0.5M Arginine, 10 mM DTT. The refolding process is continued 1 day at 8° C. without stirring.

e) Hydrophobic Batch Chromatography

The refolded protein solution was set to 1M KCl. After 30 min 5 g Butylsepharose 4 Fast Flow (Amersham Biosciences) were added and binding allowed for 1 h at 8° C. After removal of Butylsepharose by filtration the supernatant contains mainly the correctly folded active aurora protein. Under these conditions not correctly folded protein is bound to Butylsepharose. Further purification can be achieved if necessary by additional chromatography steps, e.g., ion exchange, size exclusion chromatography, etc.

f) Analysis of Refolded Protein

After refolding the supernatant of the Butyl Sepharose batch contains >90% monomeric Aurora kinase as is seen by SDS-Page and size exclusion chromatography.

Various embodiments of the invention have been described. The descriptions and examples are intended to be illustrative of the invention rather than limiting. Indeed, it will be apparent to those of skill in the art that modifications may be made to the various embodiments of the invention described without departing from the spirit of the invention or scope of the appended claims set forth below.

Each reference cited herein is hereby incorporated by reference in its entirety.

LIST OF REFERENCES

Brazil, D. P., and Hemmings, B. A., Trends Biochem. Sci. 11 (2001) 657-664
Clark, E. D., Curr. Opin. Biotechnol. 12 (2001) 202-207
Datta, S. R., et al., Genes Dev. 13 (1999) 2905-2927
Egan, S. E., and Weinberg, R. A., Nature 365 (1993) 781-783

Hardie, G., and Hanks, S., The Protein Kinase Facts Books I, Academic Press, San Diego, Calif., 1995, pp. 7-20
Hunter, T., Cell 50 (1987) 823-829
Lee, S. Y., Trends Biotechnol. 14 (1996) 98-105
Lilie, H., Current Opinion Biotechnol. 9 (1998) 497-501
Mattes, R., Semin. Thromb. Hemost. 27 (2001) 325-336
Misawa, S., and Kumagai, I., Biopolymers 51 (1999) 297-307
Panda, A. K., et al., J. Biotechnol. 75 (1999) 161-172
Thomas, S. M., and Brugge, J. S., Annu. Rev. Cell Dev. Biol. 13 (1997) 513-609 WO 2003/016516
Sambrook, et al., 1. Plasmid Vectors.
Sambrook J., Fritsch E. F, and Maniatis, T., Molecular Cloning: A Laboratory Manual, Cold Spring Harbor Laboratory Press, Cold Spring Harbor, N.Y. (1989)
Ausubel, F. M., Brent, R., Kingston, R. E., Moore, D. D., Seidman, J. G., Smith, J. A., Struhl, K., Current Protocols in Molecular Biology, Current Protocols 1987-1994 John Wiley & Sons, Inc. 1994-1998

The invention claimed is:

1. A method for the recombinant production and purification of a correctly folded protein kinase selected from the group consisting of tyrosine protein kinases and serine/threonine kinases comprising:
    a) expressing a nucleic acid encoding said protein kinase in a microbial host cell, wherein inclusion bodies containing said protein kinase are formed in said host cell,
    b) isolating said protein kinase from the cell, solubilizing said protein kinase, and then renaturing said protein kinase to provide a renatured protein kinase, and
    c) purifying said renatured protein kinase by hydrophobic interaction chromatography with a hydrophobic adsorbent wherein said renatured protein kinase is applied directly to said hydrophobic adsorbent in an aqueous solution comprising at least a 1 M salt solution wherein the cation is selected from the group consisting of sodium, potassium and ammonium, and an anion selected from the group consisting of chloride, phosphate and sulfate, except that where the cation is ammonium, the anion is not sulfate,
    whereby at least 70% of said protein kinase recovered is correctly folded and is not bound to said hydrophobic adsorbent.

2. The method according to claim 1, wherein the hydrophobic adsorbent comprises a gel matrix substituted with hydrophobic ligands in the range of 10-50 μmol/ml gel, wherein the hydrophobic ligands are selected from the group $C_2$-$C_8$ alkyl residues or simple aryl(phenyl) residues.

3. The method according to claim 2, wherein the hydrophobic adsorbent comprises a cross-linked agarose substituted with phenyl-, butyl- or octyl groups.

4. The method according to claim 3, wherein the hydrophobic adsorbent is selected from the group consisting of phenyl-, octyl- or butyl-sepharose.

5. The method of claim 1, wherein the salt is KCl or NaCl.

6. The method according to claim 1, wherein the aqueous solution comprises in addition at least 0.5 M arginine, guanidine or a compound having the general formula I $$R_2\text{—CO—NRR}_1 \quad (I),$$

or combinations thereof,
wherein
    R and $R_1$ are hydrogen or a saturated or unsaturated branched or unbranched $C_1$-$C_4$ alkyl chain and
    $R_2$ is hydrogen, $NHR_1$ or a saturated or unsaturated branched or unbranched $C_1$-$C_3$ alkyl chain.

7. A method for the recombinant production and purification a correctly folded protein kinase selected from the group consisting of a Src, a PKB, a c-Met, a Lck, an Aurora or a p38 MAPK protein kinase comprising:
    a) expressing a nucleic acid encoding said protein kinase in a microbial host cell, wherein inclusion bodies containing said protein kinase are formed in said host cell,
    b) isolating said protein kinase from the cell, solubilizing said protein kinase, and then renaturing said protein kinase to provide a renatured protein kinase, and
    c) purifying said renatured protein kinase by hydrophobic interaction chromatography with a hydrophobic adsorbent wherein said renatured protein kinase is applied directly to said hydrophobic adsorbent in an aqueous solution comprising at least a 1 M salt solution wherein the cation is selected from the group consisting of sodium, potassium and ammonium, and an anion selected from the group consisting of chloride, phosphate and sulfate, except that where the cation is ammonium, the anion is not sulfate,
    whereby at least 70% of said protein kinase recovered is correctly folded and is not bound to said hydrophobic adsorbent.

8. The method according to claim 7, wherein the hydrophobic adsorbent comprises a gel matrix substituted with hydrophobic ligands in the range of 10-50 μmol/ml gel, wherein the hydrophobic ligands are selected from the group comprising $C_2$-$C_8$ alkyl residues or simple aryl(phenyl) residues.

9. The method according to claim 8, wherein the hydrophobic adsorbent comprises a cross-linked agarose substituted with phenyl-, butyl- or octyl groups.

10. The method according to claim 9, wherein the hydrophobic adsorbent is selected from the group consisting of phenyl-, octyl- or butyl-sepharose.

11. The method of claim 7, wherein the salt is KCl or NaCl.

12. The method according to claim 7, wherein the aqueous solution comprises in addition at least 0.5 M arginine, guanidine or a compound having the general formula I $$R_2\text{—CO—NRR}_1 \quad (I),$$

or combinations thereof,
wherein
    R and $R_1$ are hydrogen or a saturated or unsaturated branched or unbranched $C_1$-$C_4$ alkyl chain and
    $R_2$ is hydrogen, $NHR_1$ or a saturated or unsaturated branched or unbranched $C_1$-$C_3$ alkyl chain.

* * * * *

UNITED STATES PATENT AND TRADEMARK OFFICE
CERTIFICATE OF CORRECTION

| | |
|---|---|
| PATENT NO. | : 7,393,936 B2 |
| APPLICATION NO. | : 11/000867 |
| DATED | : July 1, 2008 |
| INVENTOR(S) | : Hertenberger et al. |

It is certified that error appears in the above-identified patent and that said Letters Patent is hereby corrected as shown below:

Title Page, Item (73) Assignee - Delete "Hoff"

Signed and Sealed this

First Day of December, 2009

David J. Kappos
*Director of the United States Patent and Trademark Office*